(12) United States Patent
Liu et al.

(10) Patent No.: US 8,263,398 B2
(45) Date of Patent: Sep. 11, 2012

(54) PROMOTER AND VIRAL VECTOR CONTAINING THE SAME

(76) Inventors: Jin-Hwang Liu, Taipei (TW); Chin-Cheng Liu, Taipei (TW)

( * ) Notice: Subject to any disclaimer, the term of this patent is extended or adjusted under 35 U.S.C. 154(b) by 0 days.

(21) Appl. No.: 12/907,565

(22) Filed: Oct. 19, 2010

(65) Prior Publication Data

US 2011/0105595 A1 May 5, 2011

(30) Foreign Application Priority Data

Oct. 20, 2009 (TW) .............................. 98135496 A (51) Int. Cl.
*C12N 5/00* (2006.01)
*C12N 15/00* (2006.01)
*C12P 21/06* (2006.01)
*C07H 21/04* (2006.01)
*A61K 48/00* (2006.01)

(52) U.S. Cl. ........... 435/320.1; 435/69.1; 435/325; 435/455; 536/23.1; 536/24.1; 514/44 R (58) Field of Classification Search ..................... None
See application file for complete search history.

(56) References Cited

U.S. PATENT DOCUMENTS 7,026,164 B2   4/2006  Li et al.
7,109,029 B2   9/2006  Clarke et al.

OTHER PUBLICATIONS

Chin-Cheng et al. A Novel E1B-55kD-Deleted Oncolytic Adenovirus Carrying Mutant KRAS-Regulated hdm2 Transgene Exerts Specific Antitumor Efficacy on Colorectal Cancer Cells. Mol Cancer Ther. 9(2):450-60, 2010.*

Ramon Alemany, et al; "Replicative adenoviruses for cancer therapy", Nature Biotechnology, vol. 18, Jul. 2000, pp. 723-727.
Carla Heise, et al; "Replication-selective adenoviruses as oncolytic agents", J. Clin. Invest. 2000; vol. 105, pp. 847-851.
Theodore L. Deweese, et al; "A Phase I Trial of CV706, a Replication-competent, PSA Selective Oncolytic Adenovirus, for the Treatment of Locally Recurrent Prostate Cancer following Radiation Therapy", Cancer Research 61, 7464-7472, Oct. 15, 2001.
Fadlo R. Khuri, et al; "A controlled trial of intratumoral Onyx-015, a selectively-replicating adenovirus, in combination with cisplatin and 5-fluorouracil in patients with recurrent head and neck cancer", Nature Medicine, vol. 6, No. 8, Aug. 2000, pp. 879-885.
John Nemunaitis, et al; "Selective Replication and Oncolysis in p53 Mutant Tumors with Onyx-015, an E1B-55kD Gene-deleted Adenovirus, in Patients with Advanced Head and Neck Cancer: A Phase II Trial", Cancer Research 60, pp. 6359-6366, Nov. 15, 2000.
Roland L. Chu, et al; "Use of Replicating Oncolytic Adenoviruses in Combination Therapy for Cancer", Clinical Cancer Research, vol. 10, Aug. 15, 2004, pp. 5299-5312.
James R. Bischoff, et al; "An Adenovirus Mutant That Replicates Selectively In p53-Deficient Human Tumor Cells", Science, vol. 274, pp. 373-376, Oct. 18, 1996.

(Continued)

*Primary Examiner* — Sumesh Kaushal
(74) *Attorney, Agent, or Firm* — Ladas & Parry LLP (57) ABSTRACT

The invention constructs an activating KRASmutant but not p53-responsive promoter and generates an E1B-55kD-deleted (ΔE1B-55kD) adenovirus, harboring a transcriptionally activating transgene and holding lytic replication ability in the tumor cells with activating $KRAS^{mutant}$. The adenovirus of the invention can be used in the treatment of cancers.

7 Claims, 6 Drawing Sheets

OTHER PUBLICATIONS

Carla C. Heise, et al; "Intravenous Administration of Onyx-015, a Selectively Replicating Adenovirus, Induces Antitumoral Efficacy", Cancer Research 59, pp. 2623-2628, Jun. 1, 1999.

Felicia D. Goodrum, et al; "The Early Region 1B 55-Kilodalton Oncoprotein of Adenovirus Relieves Growth Restrictions Imposed on Viral Replication by the Cell Cycle", Journal of Virology, Jan. 1997, pp. 548-561, vol. 71, No. 1.

Wilma T. Steegenga, et al; "Infectivity and expression of the early adenovirus proteins are important regulators of wild-type and DeltaE1B adenovirus replication in human cells", Oncogene (1999) 18, pp. 5032-5043.

Tsun L. Chan, et al; "*BRAF* and *KRAS* Mutations in Colorectal Hyperplastic Polyps and Serrated Adenomas[1]", Cancer Research 63, pp. 4878-4881, Aug. 15, 2003.

David A. Eberhard, et al; "Mutations in the Epidermal Growth Factor Receptor and in KRAS Are Predictive and Prognostic Indicators in Patients with Non-Small-Cell Lung Cancer Treated With Chemotherapy Alone and in Combination With Erlotinib", Journal of Clinical Oncology, vol. 23, No. 25, Sep. 1, 2005, pp. 5900-5909.

Hong Zhang, et al; "Expression of oncogenes, tumour suppressor, mismatch repair and apoptosis-related genes in primary and metastatic melanoma cells", International Journal of Oncology, 19: pp. 1149-1153, 2001.

Thomas Rothmann, et al; "Replication of Onyx-015, a Potential Anticancer Adenovirus, Is Independent of p53 Status in Tumor Cells", Journal of Virology, Dec. 1998, pp. 9470-9478, vol. 72, No. 12.

Jiandong Chen, et al; "Regulation of Transcription Functions of the p53 Tumor Suppressor by the mdm-2 Oncogene", Molecular Medicine, vol. 1, No. 2, Jan. 1995, pp. 142-152.

Monika Phelps, et al; "p53-independent Activation of the *hdm2*-P2 Promoter through Multiple Transcription Factor Response Elements Results in Elevated hdm2 Expression in Estrogen Receptor α-positive Breast Cancer Cells[1]", Cancer Research 63, pp. 2616-2623, Mary 15, 2003.

Stefan Ries, et al; "Opposing Effects of Ras on p53: Transcriptional Activation of *mdm2* and Induction of p19$^{ARF}$", Cell, vol. 103, pp. 321-330, Oct. 13, 2000.

\* cited by examiner

Figure 1.

A Transgenes

B Construction of Δp53REP2

C PCR-amplified DNA Fragment Lengths

SEQUENCE LISTING

```
<160> NUMBER OF SEQ ID NOS: 16

<210> SEQ ID NO 1
<211> LENGTH: 58
<212> TYPE: DNA
<213> ORGANISM: Artificial Sequence
<220> FEATURE:
<223> OTHER INFORMATION: Synthesized DNA sequence

<400> SEQUENCE: 1
ggtcaagttc agacacgttc cgaaactgca gtaaaaggag ttaagtcctg acttgtct         58

<210> SEQ ID NO 2
<211> LENGTH: 532
<212> TYPE: DNA
<213> ORGANISM: Artificial Sequence
<220> FEATURE:
<223> OTHER INFORMATION: Synthesized DNA promoter

<400> SEQUENCE: 2
ggatggtgag gagcaggtac tggcccggca gcgagcggtc acttttgggt ctgggctctg        60
acggtgtccc ctctatcgct ggttcccagc ctctgcccgt tcgcagcctt tgtgcggttc       120
gtggctgggg gctcggggcg cggggcgcgg ggcatgggc acgtggcttt gcggaggttt        180
tgttggactg gggctaggca gtcgccgcca gggaggaggg cgggatttcg gacggctctc       240
gcggcggtgg gggtgggggt ggttcggagg tctccgcggg agttcagggt aaaggtcacg       300
ggggccgggg gctgcggggc cgcttcggcg cgggaggtcc ggatgatcgc aggtgcctgt       360
cgggtcacta gtgtgaacgc tgcgcgtagt ctgggcggga ttgggccggt tcagtgggca       420
ggttgactca gcttttcctc ttgagctcca gctgggcta tttaaaccat gcattttccc        480
agctgtgttc agtggcgatt ggagggtaga cctgtgggca cggacgcacg cc               532

<210> SEQ ID NO 3
<211> LENGTH: 25
<212> TYPE: DNA
<213> ORGANISM: Artificial Sequence
<220> FEATURE:
<223> OTHER INFORMATION: Synthesized DNA promoter

<400> SEQUENCE: 3
ctgaggtacc ggatggtgag gagca                                              25

<210> SEQ ID NO 4
<211> LENGTH: 30
<212> TYPE: DNA
<213> ORGANISM: Artificial Sequence
<220> FEATURE:
<223> OTHER INFORMATION: Synthesized primer

<400> SEQUENCE: 4
```

-continued ccccagctgg agctcaagag gaaaagctga                             30

<210> SEQ ID NO 5
<211> LENGTH: 30
<212> TYPE: DNA
<213> ORGANISM: Artificial Sequence
<220> FEATURE:
<223> OTHER INFORMATION: Synthesized primer

<400> SEQUENCE: 5
ctcttgagct ccagctgggg ctatttaaac                             30

<210> SEQ ID NO 6
<211> LENGTH: 25
<212> TYPE: DNA
<213> ORGANISM: Artificial Sequence
<220> FEATURE:
<223> OTHER INFORMATION: Synthesized primer

<400> SEQUENCE: 6
tgctagatct ggcgtgcgtc cgtgc                                  25

<210> SEQ ID NO 7
<211> LENGTH: 29
<212> TYPE: DNA
<213> ORGANISM: Artificial Sequence
<220> FEATURE:
<223> OTHER INFORMATION: Synthesized primer

<400> SEQUENCE: 7
cactcgaggt aatatttgtc tagggccgc                              29

<210> SEQ ID NO 8
<211> LENGTH: 27
<212> TYPE: DNA
<213> ORGANISM: Artificial Sequence
<220> FEATURE:
<223> OTHER INFORMATION: Synthesized primer

<400> SEQUENCE: 8
gcagatctgc ccacacattt cagtacc                                27

<210> SEQ ID NO 9
<211> LENGTH: 29
<212> TYPE: DNA
<213> ORGANISM: Artificial Sequence
<220> FEATURE:
<223> OTHER INFORMATION: Synthesized primer

<400> SEQUENCE: 9
cactcgaggt aatatttgtc tagggccgc                              29

<210> SEQ ID NO 10
<211> LENGTH: 28
<212> TYPE: DNA
<213> ORGANISM: Artificial Sequence
<220> FEATURE:
<223> OTHER INFORMATION: Synthesized primer

<400> SEQUENCE: 10
aggcgcggcc gccaacattc attcccga                               28

<210> SEQ ID NO 11
<211> LENGTH: 27
<212> TYPE: DNA
<213> ORGANISM: Artificial Sequence
<220> FEATURE:

```
<223> OTHER INFORMATION: Synthesized primer

<400> SEQUENCE: 11
gttggcggcc gccccgctga tcagcct                                      27

<210> SEQ ID NO 12
<211> LENGTH: 25
<212> TYPE: DNA
<213> ORGANISM: Artificial Sequence
<220> FEATURE:
<223> OTHER INFORMATION: Synthesized primer

<400> SEQUENCE: 12
atccggtacc tcagaagcca tagag                                        25

<210> SEQ ID NO 13
<211> LENGTH: 25
<212> TYPE: DNA
<213> ORGANISM: Artificial Sequence
<220> FEATURE:
<223> OTHER INFORMATION: Synthesized primer

<400> SEQUENCE: 13
ctgaggtacc ggatggtgag gagca                                        25

<210> SEQ ID NO 14
<211> LENGTH: 25
<212> TYPE: DNA
<213> ORGANISM: Artificial Sequence
<220> FEATURE:
<223> OTHER INFORMATION: Synthesized primer

<400> SEQUENCE: 14
tgctggatcc ggcgtgcgtc cgtgc                                        25

<210> SEQ ID NO 15
<211> LENGTH: 25
<212> TYPE: DNA
<213> ORGANISM: Artificial Sequence
<220> FEATURE:
<223> OTHER INFORMATION: Synthesized primer

<400> SEQUENCE: 15
cgccggatcc agcaggcaaa tgtgc                                        25

<210> SEQ ID NO 16
<211> LENGTH: 26
<212> TYPE: DNA
<213> ORGANISM: Artificial Sequence
<220> FEATURE:
<223> OTHER INFORMATION: Synthesized primer

<400> SEQUENCE: 16
agaaagatct ttatagacag gtcaac                                       26
```

PROMOTER AND VIRAL VECTOR CONTAINING THE SAME

FIELD OF THE INVENTION

The invention relates to an isolated nucleic acid promoter and a conditionally-replicative adenoviral vector containing the same. In particular, the isolated nucleic acid promoter comprises human double minute 2 (hdm2) P2 promoter with its p53 response elements being deleted.

BACKGROUND OF THE INVENTION

Cancer is a leading cause of death in the world and elsewhere. Depending on the type of cancer, it is typically treated with surgery, chemotherapy, and/or radiation. These treatments often fail: surgery may not remove all the cancer and metastases may occur; some cancers are resistant to chemotherapy and radiation therapy; and chemotherapy-resistant tumors frequently develop. New therapies are necessary, to be used alone or in combination with classical techniques.

One potential therapy under active investigation is treating tumors with recombinant viral vectors expressing anti-cancer therapeutic proteins. Adenoviral vectors (Ad) have proven to be of enormous utility for a variety of gene therapy applications. Adenovirus-based vectors contain several characteristics that make them conceptually appealing for use in treating cancer, as well as for therapy of genetic disorders. Adenoviruses can easily be grown in culture to high titer stocks that are stable. They have a broad host range, replicating in most human cancer cell types. Their genome can be manipulated by site-directed mutation and insertion of foreign genes regulated by foreign promoters.

Conditionally-replicative adenoviruses (CRAds) have been a novel class of anticancer agents, which are designed to selectively replicate in tumor cells and to lyse them (1-3). U.S. Pat. No. 7,109,029 discloses a viral vector, which has at least one interfering genetic element, comprising at least one transcription unit, wherein at least one insulating sequence is located 5' to the transcription initiation site of said transcription unit and 3' to said interfering genetic element. U.S. Pat. No. 7,026,164 provides adenovirus packaging cell lines for growth of an E1A/E1B deficient adenovirus that is substantially free of replication competent adenovirus (RCA). CRAd-based cancer treatments are already being evaluated in clinical trials (4-7). The safety and efficacy of CRAds depend on the specific viral replication in tumor versus in normal cells. Deleting viral genes encoding proteins required for the viral life cycle in normal cells but not in tumor cells is a strategy to induce a tumor-specific viral replicative lysis (3). This strategy has been exploited in E1B-55 kD-deleted therapeutic CRAds, which were designed to exert specific cytopathic effect on p53-nonfunctional tumor cells (8, 9). The p53 gene is one of the most studied and well-known genes. p53 plays a key role in cellular stress response mechanisms by converting a variety of different stimuli, for example, DNA damage, deregulation of transcription or replication, and oncogene transformation, into cell growth arrest or apoptosis. p53 is inactivated in a majority of human cancers. When p53 is inactivated, abnormal tumor cells are not eliminated from the cell population, and are able to proliferate. An elegant example of E1B-55 kD-deleted therapeutic CRAds is ONYX-015 (dl1520), which has shown definitive antitumour activities in p53 nonfunctional tumors (10, 11). The E1B-55 kD-deleted Ads failed to replicate efficiently in cells with $p53^{wild}$. Induction of p53 expression by E1B-55 kD-deleted Ads in normal cells is deemed to be contributory for the resistance of these cells to lytic replication of the E1B-55 kD-deleted Ads. Conversely, the lack of p53 accounts for the permissiveness of tumor cells to the lytic replication of E1B-55 kD-deleted Ads.

The human ras gene family consists of three members: the H-ras, K-ras and the N-ras gene. These genes code for related proteins of 21 kD, which are located at the inner face of the cell membrane and are thought to be involved in transducing signals from cell surface receptors to their intracellular targets. A significant portion of tumor cell lines and fresh tumor tissue has been found to possess an activated ras gene. Such genes are characterized by their ability to induce oncogenic transformation of cells. In most cases so far analyzed the activation is due to a point mutation in the 12nd or 13rd codon of a ras gene resulting in a single amino acid substitution in the gene product. Activating mutation of RAS has been implicated in tumorigenesis of many malignancies including lung cancer and colorectal cancer at rates of around 21% and 34%, respectively (12, 13). There were also many other malignancies harboring RAS activating mutations and exhibiting elevated RAF activities (14). With an aim to extend the cytopathic spectrum of CRAds to tumors with activating RAS, a strategy taking advantage of conditional sequestering of p53 in tumor cells but leave unaffected bystander normal cells bearing $p53^{wild}$ may be used. Paradoxically, it was found that an E1B-55 kD-deleted Ad could replicate in $p53^{wild}$ tumor cells (15). In these cases, Hdm2, the negative regulator of p53 might be implicated for it is transcriptionally upregulated by p53 and forms with p53 a feedback loop to inactivate p53 (16). Noticeably, the transcription of hdm2 gene could also be turned on by the RAS-upregulated RAF/MEK/MAPK pathway, in a p53-independent manner (17). A Ras/Raf signaling cascade-responsive element composed of ETSA and AP-1/ETSB elements was identified in the mouse double minute 2 (mdm2) P2 promoter, just upstream of the p53 responsive promoter elements (17, 18). The hdm2 P2 promoter is composed of AP-1/ETSa, which are the conserved homologues of AP-1/ETSB in mdm2 P2 promoter; however, does not include the counterpart of ETSA element in mdm2 P2 promoter. Nonetheless, Ras/Raf signaling cascade-responsiveness of the hdm2 P2 promoter was indeed found in human cancer cells (17).

Thus, there is a continuing need for vectors that replicate and spread efficiently in tumors but that can be modified such that they replicate poorly or not at all in normal tissue.

SUMMARY OF THE INVENTION

The invention provides an isolated nucleic acid promoter, comprising human double minute 2 (hdm2) P2 promoter with a part of or total of p53 response elements being deleted. The preferred promoter is Δp53REP2 promoter.

The invention provides a viral vector, comprising the promoter of the invention.

The invention also provides a conditionally-replicative adenoviral vector, comprising Δp53REP2 promoter of the invention, Hdm2-encoding DNA located at downstream of and operably linked to the Δp53REP2 promoter and the encoding DNAs of E1A and E1B-19 kD but not E1B-55 kD.

The invention further provides a method for treating cancer comprising administering to a subject in need of such therapy a therapeutically effective amount of a conditionally-replicative adenoviral vector of the invention.

The invention also further provides a pharmaceutical composition, comprising a conditionally-replicative adenoviral vector of the invention pharmaceutically acceptable carriers.

BRIEF DESCRIPTION OF THE DRAWING

FIG. 4 shows the plaque forming assay of the adenoviral vectors. A, The plaque formed on cell line culture infected with adenoviral vectors. For each cell line, 10⁶ cells were seeded in each 60 mm dish, and the cytopathic effect (CPE) manifested as plaque-forming units was evaluated 7 days after 1-h Ad infection at MOI of 10-4. Plaques were counted after staining with 1 ml of the 0.03% neutral red solution for each dish. B, The number of plaque-forming units (pfus) of cell lines transduced with mock-Ad (supernatant of HEK293 cell culture), Ad-E1, Ad-Dp53REP2, or Ad-KRhdm2, were presented as mean±SE of triplicates of three independent experiments.

FIG. 6 shows cytopathic effect s of Ad-KRhdm2 and controls injected intratumorally in nude mouse xenograft model. Xenografts in nude mice were established as described in Materials and Methods. Eight xenografts from each of the RKO, LoVo, SW620, and LS174T cell lines on 4 nude mice were grown to 100 mm³ and at that time were intratumorally injected with $10^{10}$ pfus of each of Ad-E1, Ad-ΔE1B55 kD or Ad-hMDM2 vevctors, or PBS (four mice per group). Mean tumor volumes (±SE) were monitored and measured as described in Materials and Methods every 5 days after Ad injection. Mice were sacrificed when the tumors were too large to bear (around 2500 mm³).

DETAILED DESCRIPTION OF THE INVENTION

The invention constructs an activating mutant KRAS but not p53-responsive promoter and generates a conditionally-replicative viral vector, harboring a transcriptionally activating transgene and holding lytic replication ability in the tumor cells with activating $KRAS^{mutant}$. The adenovirus of the invention can be used in the treatment of cancers.

As used herein, the terms "a" and "an" are used to refer to both single and a plurality of objects.

Promoter of the Invention

In one aspect, the invention provides an isolated nucleic acid promoter comprising human double minute 2 (hdm2) P2 promoter with a part of or total of p53 response elements being deleted.

The term "isolated," when referring to a molecule, such as a promoter sequence, means that the molecule is separated from at least one other compound, such as a protein, DNA, RNA, or other contaminants with which it is associated in vivo or in its naturally occurring state. Thus, a nucleic acid sequence is considered isolated when it has been isolated from any other component with which it is naturally associated. The term "naturally occurring" or "wild type" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

The term "nucleic acid" or "nucleic acid sequence," refers to a nucleotide, oligonucleotide, polynucleotide, or any fragment thereof.

The term "promoter" refers to an untranslated DNA sequence usually located upstream of the coding region that contains the binding site for RNA polymerase II and initiates transcription of the DNA. The promoter region may also include other elements that act as regulators of gene expression.

In the present invention, the promoter gene is derived from human double minute 2 (hdm2) P2 promoter wherein its p53 response elements are deleted. The hdm2 P2 promoter (Δp53REP2 promoter) contains both RAS/RAF pathway response element and two p53 response elements. According to the invention, the DNA sequences 448 to 505 (GGT CAAGTTCAGA CACGTTCCGA AACTGCAGTA AAAG-GAGTTA AGTCCTGACT TGTCT; SEQ ID NO:1) at the hdm2 P2 promoter are deleted and the new constructed promoter is named as Δp53REP2 promoter. A promoter DNA derived from Δp53REP2 promoter could be modified by deleting a part of it as long as the promoter activity has similar activity to Δp53REP2 promoter. According to one embodiment of the invention, the Δp53REP2 promoter of the present invention may be around 574 bp long. One preferred embodiment of the promoter of the invention has the following sequence:

tors of the invention include, but are not limited to, DNA, DNA encapsulated in an adenovirus coat, adenoviral DNA packaged in another viral or viral-like form (such as herpes simplex, and AAV), adenoviral DNA encapsulated in liposomes, adenoviral DNA complexed with polylysine, adenoviral DNA complexed with synthetic polycationic molecules, conjugated with transferrin, or complexed with

```
                                                          (SEQ ID NO: 2)
  1 GGATGGTGAG GAGCAGGTAC TGGCCCGGCA GCGAGCGGTC ACTTTTGGGT

51 CTGGGCTCTG ACGGTGTCCC CTCTATCGCT GGTTCCCAGC CTCTGCCCGT

101 TCGCAGCCTT TGTGCGGTTC GTGGCTGGGG GCTCGGGGCG CGGGGCGCGG

151 GGCATGGGGC ACGTGGCTTT GCGGAGGTTT TGTTGGACTG GGGCTAGGCA

201 GTCGCCGCCA GGGAGGAGGG CGGGATTTCG GACGGCTCTC GCGGCGGTGG

251 GGGTGGGGGT GGTTCGGAGG TCTCCGCGGG AGTTCAGGGT AAAGGTCACG

301 GGGGCCGGGG GCTGCGGGGC CGCTTCGGCG CGGGAGGTCC GGATGATCGC

351 AGGTGCCTGT CGGGTCACTA GTGTGAACGC TGCGCGTAGT CTGGGCGGGA

401 TTGGGCCGGT TCAGTGGGCA GGTTGACTCA GCTTTTCCTC TTGAGCTCCA

451 GCTGGGGCTA TTTAAACCAT GCATTTTCCC AGCTGTGTTC AGTGGCGATT

501 GGAGGGTAGA CCTGTGGGCA CGGACGCACG CC
```

Conditionally-Replicative Adenoviral Vector of the Invention

In an aspect, the invention also provides a viral vector, comprising the promoter of the invention (preferably, the Δp53REP2 promoter). According to the invention, the viral vector is an adenovirus, adeno-associated virus, vaccinia virus, retrovirus, lentivirus or herpes simplex virus.

According to one embodiment of the invention, the invention also provides a conditionally-replicative adenoviral vector, comprising the promoter of the invention (preferably, the Δp53REP2 promoter). According to a further embodiment of the invention, the conditionally-replicative adenoviral vector comprises Δp53REP2 promoter, Hdm2-encoding DNA located at downstream of and operably linked to the Δp53REP2 promoter and the encoding DNAs of E1A and E1B-19 kD but not E1B-55 kD.

The term "conditionally-replicative" refers to the expression of a viral gene or the replication of a virus or a vector, wherein the expression of replication is dependent (i.e., conditional) upon the presence or absence of specific factors in the target cell.

The term "operably linked" refers to functionally related nucleic acid sequences. A promoter is operably linked with a coding sequence if the promoter controls the translation of the encoded polypeptide.

The terms "adenovirus" and "adenoviral particle" as used herein include any and all viruses that may be categorized as an adenovirus, including any adenovirus that infects a human or an animal, including all groups, subgroups, and serotypes. Thus, as used herein, "adenovirus" and "adenovirus particle" refer to the virus itself or derivatives thereof and cover all serotypes and subtypes and both naturally occurring and recombinant forms. In one embodiment, such adenoviruses infect human cells. Such adenoviruses may be wildtype or may be modified in various ways known in the art or as disclosed herein. Such modifications include modifications to the adenovirus genome that is packaged in the particle in order to make an infectious virus. Exemplary adenoviral veccompounds such as PEG to immunologically "mask" the antigenicity and/or increase half-life, or conjugated to a non-viral protein.

According to the invention, the "E1A" refers to coding all gene products of the adenovirus E1A region, including expression products of the two major RNAs: 13S and 12S. These are translated into polypeptides of 289 and 243 amino acids, respectively. These two proteins differ by 46 amino acids, which are spliced from the 12S mRNA. The encoding nucleic acid sequence of E1A in the conditionally-replicative adenoviral vector of the invention refers to E1A coding sequence and its variants.

According to the invention, the "E1B" refers to all gene products of the adenovirus E1B region, including the 3 major polypeptides, of 19 kd and 55 kd. The E1B 19 kd and 55 kd proteins are important in cell transformation. In the conditionally-replicative adenoviral vector of the invention, the E1B-19 kd but not E1B-55 kD coding sequence is contained. The encoding nucleic acid sequence of E1B-19 kD but not E1B-55 kD in the conditionally-replicative adenoviral vector of the invention refers to E1 B-19 kd but not E1B-55 kD coding sequence and its variants.

The conditionally-replicative adenoviral vector of the invention selectively replicates in and exertes cytopathic effects on cancer cells with activating RAS, irrespective of p53 gene status by forming plaques and exhibiting cytotoxicities in cells. The conditionally-replicative adenoviral vector of the invention, like other E1B-55 kD-deleted adenovirus, also exerted selective cytopathic effects on tumor cells with loss-of-function p53 mutant.

The viral vector of the invention can be prepared by using recombinant DNA technology. The "recombinant DNA technology" refers to techniques for uniting two or more DNA molecules. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

The invention described herein encompasses a method for treating cancer comprising administering to a subject in need of such therapy a therapeutically effective amount of a viral vector of the invention. Accordingly, the viral vector of the invention can be used to modulate the development and progression of cancer, which includes, but is not limited to, neoplasms, tumors, carcinomas, sarcomas, adenomas, myeloid lymphomas, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leimyosarcoma, rhabdotheliosarcoma, colon carcinoma, pancreatic cancer, liver cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependynoma, pinealoma, hemangioblastoma, retinoblastoma, leukemia (e.g. acute lymphocytic leukemia), acute myelocytic leukemia (myelolastic, promyelocytic, myelomonocytic, monocytic and erythroleukemia), chronic leukemia (chronic myelocytic (granulocytic) leukemia and chronic lymphocytic leukemia), polycythemia vera, lymphoma (Hodgkin's disease and non-Hodgkin's diseases), multiple myeloma, Waldenstrom's macroglobulinemia, rectal carcinoma, head and neck cancer, brain cancer, cancers of unknown primary site, cancers of the peripheral nervous system, cancers of the central nervous system, acoustic neuroma, oligodendroglioma, meningioma, neuroblastoma, heavy chain disease, metastases, and any disease or disorder characterized by uncontrolled or abnormal cell growth. Preferably, the cancer is lung carcinoma, small cell lung carcinoma, colon carcinoma or rectal carcinoma.

In an embodiment, the viral vector of the invention is administered by direct injection into the tumor or cancerous tissue. In another embodiment, the viral vector or the conditionally-replicative adenoviral vector of the invention is administered by systemic administration (e.g., intravenous infusion). In yet another embodiment, the conditionally-replicative adenoviral vector of the invention is administered into the lumen of a tissue or organ (e.g., intravesically).

In yet another embodiment of the invention, the viral vector of the invention may be used in combination with radiation therapy. The radiation therapy can be any form of radiation therapy used in the art such as for example, external beam radiation such as x-ray treatment, radiation delivered by insertion of radioactive materials within the body near or at the tumor site such as treatment with gamma ray emitting radionuclides, particle beam therapy which utilizes neutrons or charged particles and the like. In addition, this embodiment encompasses the use of more than one of the vectors of the present invention in a cocktail in combination with radiation therapy.

Another embodiment of the invention involves the use of the viral vector of the invention in combination with chemotherapy. Chemotherapeutic agents are known in the art and include antimetabolites including pyrimidine-analogue and purine-analogue antimetabolies, plant alkaloids, antitumor antibiotics, alkylating agents and the like. The use of more than one of the vectors of the present invention with a chemotherapeutic agent or agents is also contemplated within this embodiment.

The viral vector of the invention exhibits specific cytopathic effects on tumor cells with activating $KRAS^{mutant}$ and also on tumors with $p53^{mutant}$. It targets to tumor cells with activating $KRAS^{mutant}$, irrespective of their p53 gene status but no apparent cytopathic effect is shown on neighboring normal cells. Therefore, the conditionally-replicative adenoviral vector of the invention has tumor-selectivity. The conditionally-replicative adenoviral vector of the invention also inactives p53 to exert replicative lysis. The viral vector of the invention can be used as anti-cancer agents.

Pharmaceutical Composition

In another aspect, the invention provides a pharmaceutical composition, comprising a viral vector of the invention and pharmaceutically acceptable carriers.

The pharmaceutical compositions of the present invention can be administered by any suitable route known in the art including for example by direct injection into a tumor or by other injection routes such as intravenous, subcutaneous, intramuscular, transdermal, intrathecal and intracerebral. Administration can be either rapid as by injection or over a period of time as by slow infusion or administration of slow release formulation.

Compositions according to the invention can be employed in the form of pharmaceutical preparations. Such preparations are made in a manner well known in the pharmaceutical art. One preferred preparation-utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion into the cerebrospinal fluid by continuous or periodic infusion.

It is also contemplated that certain compositions containing conditionally-replicative adenoviral vector of the invention are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art.

The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE

Example 1

Materials and Methods

Cell Lines and Culture

The HEK293 human embryonic kidney cell line, the normal MRC-5 human fetal lung fibroblast and the RKO, HCT116, LoVo, LS174T, LS123, SW620, and HT29 human colorectal cancer cell lines, were obtained from American Type Culture Collection (ATCC, Manassas, Va.). The statuses of p53 and KRAS genes of the above cell lines can be referred to "the catalogue of somatic mutations in cancer, in The Sanger Institute COSMIC database", on the website of www.sanger.ac.uk. MRC5 and RKO lines harbor KRASwild and p53wild genes; HCT116, LoVo, and LS174T cell lines harbor G13D, G13D, and G12D KRASmutant genes, respectively, and p53wild gene; LS123, SW620 and, H129 harbor G12S, G13V, and G61L KRASmutant genes, respectively, and p53mutant gene. HEK293 cells were cultured in Eagle's minimum essential medium supplemented with 2 mM L-glutamine, 0.1 mM non-essential amino acids, 1 mM sodium pyruvate, and 10% heat-inactivated horse serum. RKO and MRC-5 cells were maintained in Eagle's minimum essential medium with 10% heat-inactivated fetal bovine serum (FBS). HCT116 and HT29 cells were cultured in McCoy's 5A medium with 1.5 mM L-glutamine, and 10% heat-inactivated FBS. LoVo cells were maintained in Ham's F12K medium with 2 mM L-glutamine and 10% heat-inactivated FBS. LS174T and LS123 cells were maintained in Eagle's minimum essential medium with 2 mM L-glutamine, 0.1 mM non-essential amino acids, 1 mM sodium pyruvate and 10% heat-inactivated FBS. SW620 cells were maintained in Leibovitz's L-15 medium with 2 mM L-glutamine and 10% heat-inactivated FBS. All cells were kept at 37° C. in a 5% $CO_2$ humidified atmosphere.

Construction and Reporter Activities of the Activating KRASmutant-Responsive hmd2 Δp53REP2 Promoter The hmd2 P2 promoter contains both RAS/RAF pathway and two p53 response elements. The pΔp53REP2-Luc reporter vector was created by overlap extension PCR mutation to splice the two p53 respond elements from hmd2 P2 promoter region (FIG. 1B) (19), and then inserted into pGL3-Basic plasmid (Promega, Madison, Wis.), which contains the firefly luciferase reporter. Two sets of primers used to amplify the p53 REs-deleted P2 fragment are primer P2-KpnI-F: 5'-CTGAGGTACCGGATGGTGAGGAGCA-3' (SEQ ID NO:3), and primer P2-INT-R: 5'-CCCCAGCTGGAGCT-CAAGAGGAAAAGCTGA-3 (SEQ ID NO:4); and primer P2-INT-F: 5'-CTCTTGAGCTCCAGCTGGGGCTATT-TAAAC-3' (SEQ ID NO:5), and primer P2-BglII-R: 5'-TGCTAGATCTGGCGTGCGTCCGTGC-3' (SEQ ID NO:6). The two internal primers, primers P2-INT-F and P2-INT-R, have overlapping homologous regions with the two p53 response elements being spliced while the other two primers, primers P2-KpnI-F and P2-BglII-R, flank the P2 region and incorporate a restriction site in either sequence. Two separate PCR reactions were run, using primers P2-KpnI-F and P2-INT-R, and primers P2-INT-F and P2-BglII-R to amplify separate, overlapping sequences of the p53 RE-lacking P2 (Δp53REP2) regions. Following amplification, the primers were removed and the PCR products were denatured and re-annealed. Overlapped duplex were then PCR-extended to full length using primers P2-KpnI-F and P2-BglII-R. After restriction-digested, the Δp53REP2 fragments were cloned into pGL3-Basic vector to form the pΔp53REP2-Luc reporter vector. The pp21Cip1-Luc reporter plasmid contains the firefly luciferase gene driven by heat shock protein minimum TATA promoter sequence and two copies of p53 response elements. The control plasmid, pCMVΔ, carries the β-galactosidase gene driven by the CMV promoter (Clontech, Mountain View, Calif.).

Luciferase-Reporter Activity Assay

The relative luciferase activities of p53-dependent p21Cip1 promoter and KRAS-dependent hdm2 P2 promoter in each cell line was determined using the Dual-Luciferase® Reporter Assay System (Promega, Madison, Wis.) 48 hrs after transfection with pp21Cip1-Luc, pΔp53REP2-Luc, and pGL3-Basic (as negative control) plasmids. Transfection efficiency was normalized with the activity of β-galactosidase reported by pCMVβ, which was cotransfected with the aforementioned pGL3-luciferase-reporter constructs. To test the reporter activities of the p53-dependent p21Cip1 promoter and the KRAS-dependent Δp53REP2 promoter, $5 \times 10^5$ cells were plated per 60-mm dish, harvested 48 h after transfection using SuperFect® transfection reagent (Qiagen, Hilden, Germany) according to the manufacturer's instructions with 4.5 μg of the pΔp53REP2-Luc, the pp21Cip1-Luc, or pGL3-Basic, and 0.5 μg of pCMVβ. The cells harvested were then processed for Dual-Luciferase® Reporter Assay System (Promega, Madison, Wis.) and the β-Gal assay (Invitrogen, Carlsbad, Calif.). The luciferase activity was normalized against the β-galactosidase activity to equalize transfection efficiency.

Construction and Packaging of Adenoviral Vectors

Figure 1:
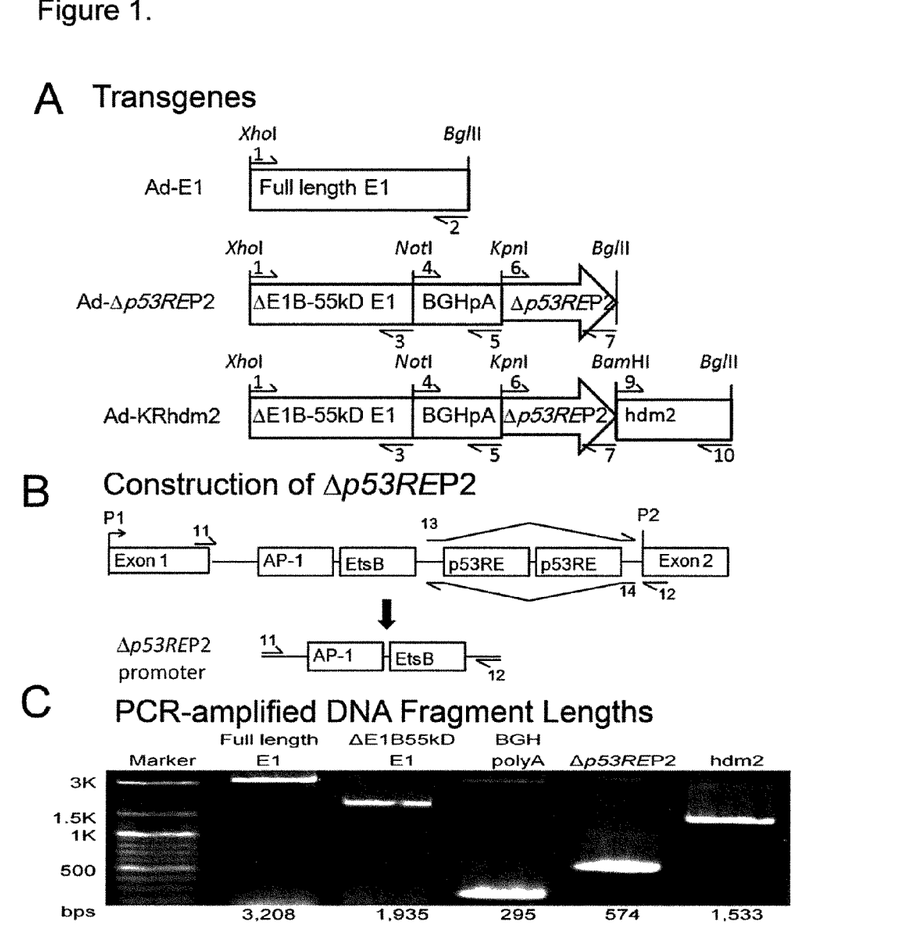
FIG. 1 shows Hdm2 transgene under control of the activating mutant KRAS-responsive promoter and the controls to be constructed into shuttle plasmids for packaging of adenoviral vectors. A, Transgenes to be inserted in shuttle plasmids for generating Ad-E1, Ad-Δp53REP2 and Ad-KRhdm2 adenoviral vectors. The Ad-E1 adenoviral vector contains full length E1-encoding sequence of adenovirus 5; the Ad-Δp53REP2 adenoviral vector contains E1A to E1B19K-encoding sequence and a Δp53REP2 promoter-driven empty cassette; and the Ad-KRhdm2 adenoviral vector carrying all DNA elements of the Ad-Δp53REP2 adenoviral vector and in addition the Hdm2 cDNA driven by the Δp53REP2 promoter. B, The schematic constructs of the Δp53REP2 promoter. In A and B, positions of primers are shown and their sequences are listed in Materals and Methods. Primers: 1, E1-337-XhoI-F; 2, E1-3528-BglII-R; 3, E1-2150-NotI-R; 4, BpA-NotI-F; 5, BpA-KpnI-R; 6, P2-KpnI-F; 7, P2-BglII-R; 8, P2-BamHI-R; 9, H2-BamHI-F; 10, H2-BglII-R; 11, P2-KpnI-F; 12, P2-BglII-R; 13, P2-INT-F; 14, P2-INT-R. C, Fragment lengths in constructs of transgenes were examined by PCR fragment length and direct sequencing. PCR fragments were resolved in 1% agarose gel. Fragment lengths: 3208 bps for Ad5 E1, 1935 bps for ΔE1B-55kD E1 (E1A to E1B-19kD), 295 bps for the polyadenylation signal of bovine growth hormone gene, 574 bps for the Δp53REP2 promoter, and 1533 bps for Hdm2 encoding DNA.

The adenoviral vectors were constructed by homologous recombination of a shuttle plasmid carrying the transgene of interest with E1-deleted adenovirus 5 genome using the AdEasy™ Adenoviral Vector system (Stratagene, Cedar Creek, Tex.). As shown in FIG. 1A, the shuttle plasmid to make the replication competent Ad-E1 adenoviral vector contains full length E1-encoding sequence of adenovirus 5; the shuttle plasmid to make the Ad-Δp53REP2 bearing E1B-55 kD-deleted E1 with E1A and E1B-19 kD being reserved, and carrying a Δp53REP2-driven empty transgene. The shuttle plasmid to make the Ad-KRhdm2 vector contains all elements to make the Ad-Δp53REP2 and in addition the Hdm2-encoding sequence driven by the Δp53REP2 promoter. The Ad5-E1 and ΔE1B-55 kD E1 (E1A to E1B19 kD)-encoding DNAs were PCR-amplified (3208 bps and 1935 bps respectively, FIG. 1C) from HEK293 cells genomic DNA with primer set of E1-337-XhoI-F, 5'-CACTCGAGG-TAATATTTGTCTAGGGCCGC-3' (SEQ ID NO:7), and E1-3528-BglII-R, 5'-GCAGATCTGCCCACA-CATTTCAGTACC-3' (SEQ ID NO:8), and primer set of E1-337-XhoI-F, 5'-CACTCGAGG-TAATATTTGTCTAGGGCCGC-3' (SEQ ID NO:9), and E1-2150-NotI-R, 5'-AGGCGCGGCCGCCAACATTCAT-TCCCGA-'3 (SEQ ID NO:10). The polyadenylation signal of bovine growth hormone gene (295 bps, FIG. 1C) was derived from pGlow-TOPO plasmid (Invitrogen, Carlsbad, Calif.) using primer set of BpA-NotI-F: 5'-GTTGGCGGCCGC-CCCGCTGATCAGCCT-3' (SEQ ID NO:11) and BpA-KpnI-R: 5'-ATCCGGTACCTCAGAAGCCATAGAG-3 (SEQ ID NO:12). The hdm2 Δp53REP2 promoter (574 bps, FIGS. 1B and C) was derived from pΔp53REP2-Luc vector using primer set of P2-KpnI-F, 5'-CTGAGGTACCGGATG-GTGAGGAGCA-3' (SEQ ID NO:13) and P2-BamHI-R, 5'-TGCTGGATCCGGCGTGCGTCCGTGC-3' (SEQ ID NO:14). The hdm2-encoding DNA (1533 bps, FIG. 1C) was amplified from MRC5 mRNA by RT-PCR using primer set of Hdm2-BamHI-F, 5'-CGCCGGATCCAGCAGGCAAAT-GTGC-3' (SEQ ID NO:15), and Hdm2-BglII-R, 5'-AGAAA-GATCTTTATAGACAGGTCAAC-3' (SEQ ID NO:16). After restrictive digestion, the DNA fragments were cloned into the shuttle vector. The reconstructed shuttle vectors were then linearized for homologous recombination with in E. coli strain BJ5183. The reconstructed shuttle vectors were then linearized and cotransfected into E. coli strain BJ5183 together with E1-deleted adenovirus 5 genome. After in vivo homologous recombination, the adenoviral vectors were constructed. Purified recombinant adenoviral vectors were digested with PacI, and then used to transfect HEK293 cells where deleted viral assembly genes were complemented in vivo. All of the viruses were purified with Adeno-XTM virus purification kits (Clontech) according to the manufacturer's protocol. Virus titer was determined by plaque-forming unit (pfu) on the HEK293 cells. Human adenovirus type 5 DNA accession number: AC000008; hdm2 DNA accession number: AF527840.

Western Blot Analysis

The cell lysate from each sample was subjected to SDS-PAGE and then transferred to a nitrocellulose transfer membrane (Schleicher & Schuell, Dassel, Germany). The membranes were incubated with primary antibodies: anti-α-tubulin (DM1A) monoclonal antibody, (Calbiochem, Darmstadt, Germany), anti-Hdm2 (D12) monoclonal antibody (Santa Cruz Biotechnology, Santa Cruz, Calif.), anti-p14ARF (4C6/4) monoclonal antibody (Cell Signaling, Danvers, Mass.) monoclonal antibody, and anti-adenovirus hexon (3G 10) monoclonal antibody (Santa Cruz). The membranes were also incubated with alkaline phosphotase conjugated secondary antibody (Promega, Madison, Wis.), and then visualized by Lumi-Phos™ WB kit (Thermo Scientific, Waltham, Mass.).

Cell Viability Assay

To evaluate the oncolytic effect on tumor cells of the adenoviral vectors, 104 cells were seeded in 96-well plates 24 h before addition of a series of adenoviral vectors at increasing doses (MOIs of 0.01, 0.1, 1, 10, 100 and 1,000). After 7-day incubation, cell viability was determined by using TACS™ MTT assay (R&D Systems, Minneapolis, Minn.). The percent survival rate of untreated cells was assumed to be 100%.

Plaque Assay

The plaque assays were performed to determine the virus yield and the oncolytic activity of the adenoviral vectors. $10^6$ cells were seeded in 60 mm dish, and 24 h later, 1 ml of viral vectors at serial dilutions were added to the medium. After incubation of the cells in a humidified 5% $CO_2$ incubator for 2 h at 37° C., 4 ml of 0.65% Noble agar (BD Difco, Loveton Circle Sparks, Md.) dissolved in MEM, 2% PBS solution was added to each dish. Plaques were counted after 7 days by adding 1 ml of the 0.03% neutral red solution to improve the visibility.

Evaluation of Tumorocidal Effects of Intrtumorally-Injected Ad Vectors in Nude Mouse Xenograft Model Six-week old Balb/c Nude mice were purchased from Bio-LASCO (Taiwan). All animal experiments were performed in accordance with institutional guidelines approved by the Animal Care Committee of Taipei Veterans General Hospital. Five million cells of each of the RKO, LoVo, SW620, and LS174T colorectal cancer cell lines were inoculated subcutaneously into bilateral flanks of nude mice in 200 μl of DMEM. The tumor growth was assessed by measuring two dimensional diameters every 7 days with calipers. The tumor volume was determined by the simplified formula: (W2×L)/2 (21). When the tumor volume reached approximately 100 mm3, 4 mice were randomly assigned to each of the four treatment groups, njected intratumorally with PBS (negative control), Ad-KRhdm2, Ad-Δp53REP2 (the Hdm2-negative control), or Ad-E1 vectors (the E1B-55 kD-positive control). Each xenograft was intratumoarlly injected with a single injection of adenoviral vector at $10^{10}$ pfus suspended in 100 μl of PBS.

The following examples were conducted according to the materials and methods stated above.

Example 2

Construction of Adenoviral Vectors

The transgenes of Ad-E1, Ad-Δp53REP2 and Ad-KRhdm2 as shown in FIG. 1A were incorporated into their corresponding shuttle plasmids for construction of Ad vectors. The transgene insert of Ad-E1 vector carried the full length E1-encoding DNA of Ad 5 was used to construct the replication competent Ad-E1. The transgene insert of Ad-Δp53REP2 vector contained the E1A and E1B-19kD-encoding DNAs but not E1B-55 kD-encoding DNA, and the Δp53REP2 promoter-driven empty cassette, where Δp53REP2 promoter was derived from hdm2 P2 promoter with two p53 response elements being deleted (FIG. 1B). The transgene insert of the Ad-KRhdm2 vector was constructed by incorporating into that of the Ad-Δp53REP2 downstream of the Δp53REP2 promoter the Hdm2-encoding DNA. Analyses with both PCR fragment lengths (FIG. 1C) and DNA sequencing confirmed the correct construct and sequences of these transgene inserts. The ETSA site of mdm2-P2 promoter was not conserved in Δp53REP2 promoter and the two p53 response elements were deleted. The sequences of the Δp53REP2 promoter are shown below (SEQ ID NO:2):

```
  1 GGATGGTGAG GAGCAGGTAC TGGCCCGGCA GCGAGCGGTC ACTTTTGGGT

51 CTGGGCTCTG ACGGTGTCCC CTCTATCGCT GGTTCCCAGC CTCTGCCCGT

101 TCGCAGCCTT TGTGCGGTTC GTGGCTGGGG GCTCGGGGCG CGGGGCGCGG

151 GGCATGGGGC ACGTGGCTTT GCGGAGGTTT TGTTGGACTG GGGCTAGGCA

201 GTCGCCGCCA GGGAGGAGGG CGGGATTTCG GACGGCTCTC GCGGCGGTGG

251 GGGTGGGGGT GGTTCGGAGG TCTCCGCGGG AGTTCAGGGT AAAGGTCACG

301 GGGGCCGGGG GCTGCGGGGC CGCTTCGGCG CGGGAGGTCC GGATGATCGC

351 AGGTGCCTGT CGGGTCACTA GTGTGAACGC TGCGCGTAGT CTGGGCGGGA

401 TTGGGCCGGT TCAGTGGGCA GGTTGACTCA GCTTTTCCTC TTGAGCTCCA

451 GCTGGGGCTA TTTAAACCAT GCATTTTCCC AGCTGTGTTC AGTGGCGATT

501 GGAGGGTAGA CCTGTGGGCA CGGACGCACG CC
```

Figure 2:
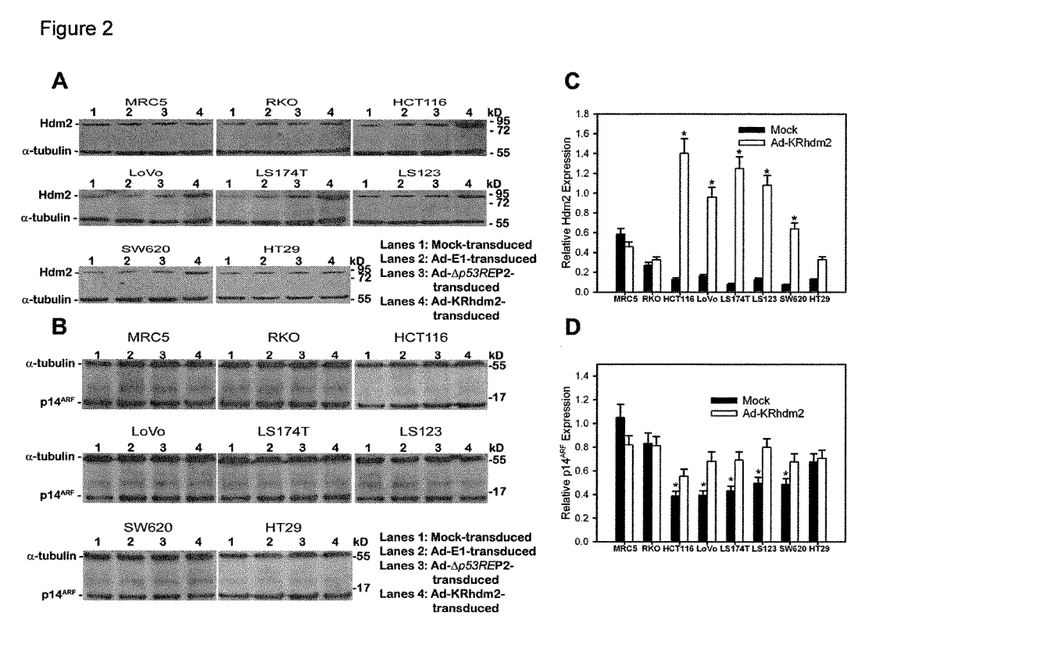
FIG. 2 shows Western blot analyses of Hdm2 and p14ARF expression in cell lines transduced with Ad-KRhdm2 and controls. A, The representative Western blots for analyses of Hdm2 and B, of p14ARF. Proteins were extracted from each cell line 2 days after 1-hour infection at MOI of 1.0 with Ad-E1, Ad-Δp53REP2, or Ad-KRhdm2 vectors. As a loading control, α-tubulin protein was also analyzed in each experimental panel. C, The intensities of Hdm2 and D, of p14ARF normalized by the corresponding intensities of α-tubulin were presented as mean±SE from 3 indepndent experiments. *, $p<0.05$ by the Mann-Whitney test.

Successful transduction with Ad-KRhdm2 was evident in addition, by Hdm2 expression (FIG. 2A).

Example 2

Figure 3:
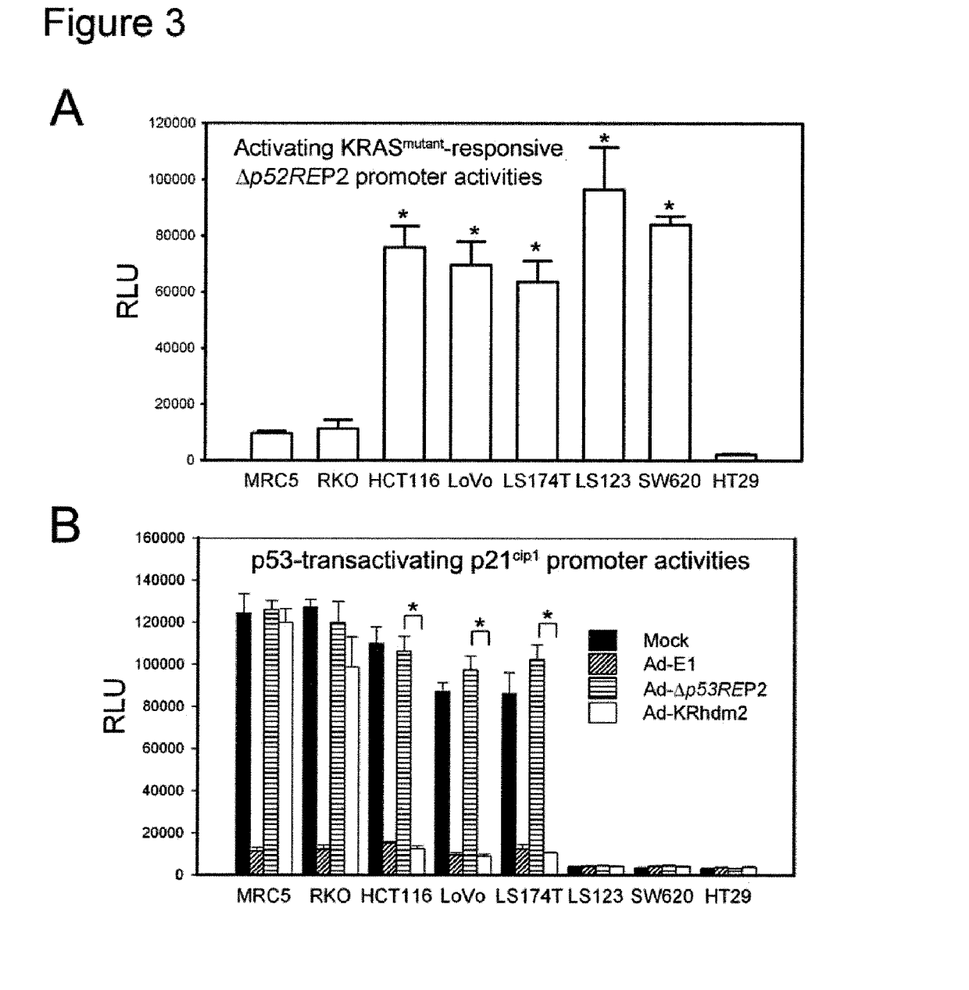
FIG. 3 shows the luciferase reporter activities of activating KRASmutant-responsive promoter and p53-transactivating p21Cip promoter. A, Reporter activity of the KRAS but not p53-responsive Δp53REP2 promter and B, p53-transactivating p21Cip1 promoter activities in each indicated cell line. To determine luciferase activities, 4.5 μg of pΔp53REP2-Luc (A) or pp21Cip1-Luc (B) reporter plasmid, and 0.5 μg of pCMVβ reporter plasmid were cotransfected into 5×10⁵ of the indicated cell line. Luciferase activity was measured 48 h post-transfection. The luciferase activities were normalized against the corresponding β-galactosidase activity to present as relative luminescence units (RLU). Data are presented as mean±SE of triplicates of three independent experiments. *$p<0.01$ by the Mann-Whitney test.

Hdm2 Expression in Ad-KRhdm2-Transduced Cells is Responsive to Activating KRAS$^{mutant}$ Irrespective of p53 Gene Status Hdm2 expression increased significantly in Ad-KRhdm2-transduced HCT116, LoVo, LS174T, LS123 and SW620 cell lines with KRAS gene mutations at either codon 12 or 13 as compared with that in MRC5 normal fibroblast or in RKO tumor cells with wild KRAS (FIGS. 2A and C). However, Hdm2 expression did not increase significantly in Ad-KRhdm2-transduced HT29 cells, which harbor G61L KRAS mutation and failed to transactivate the hdm2 Δp53REP2 promoter significantly (FIGS. 2A and C, and FIG. 3A). The increased Hdm2 expression occurred to Ad-KRhdm2-transduced HCT116, LoVo and LS 174T cell lines with p53$^{wild}$, and LS 123 and SW620 cell lines with p53$^{mutant}$. Hdm2 expression did not incrase in cells transduced with Ad-Δp53REP2, which was the negative control.

Example 3

Expression of p14$^{ARF}$ is Relatively Low in Tumor Cells with Activating KRAS$^{mutant}$ and Increases on Ad Transduction p14$^{ARF}$ expression was significantly low in HCT116, LoVo, LS174T, LS123 and SW620 cell lines harboring KRAS activating mutations in comparison to that in MRC5 normal fibroblast or in RKO tumor cells with wild KRAS (FIGS. 2B and D). p14$^{ARF}$ expression in cell lines with KRAS activating mutations but not in MRC5 or RKO cells increased on Ad infection, however only to an extent not exceeding the level in MRC5 or RKO cells infected with Ad-KRhdms (FIGS. 2B and D).

Example 4

Transactivation of Hdm2 Δp53REP2 Promoter is Responsive to Activating KRAS$^{mutant}$ Irrespective of p53 Gene Status Report assay was conducted to determine the responsiveness of hdm2 Δp53REP2 promoter activities to KRAS of various gene statuses. To do this, the Δp53REP2 promoter reporter plasmids were transfected into the indicated cell lines shown in FIG. 3A. The hdm2 Δp53REP2 promoter activities increased 6 to 9 times in HCT116, LoVo, LS174T, LS123, and SW620 cell lines with KRAS activating mutations in comparison with those in MRC5 fibroblast or in RKO cells with KRAS$^{wild}$. However, KRAS with G61L mutation in HT29 cells failed to transactivate the hdm2 Δp53REP2 promoter significantly.

Example 5

Transactivation of p21$^{Cip1}$ Promoter by p53 is Abolished by Activating KRAS$^{mutant}$-Responsive Expression of Hdm2

Shown in FIG. 3B is that p53$^{wild}$ (as in mock-transduced MRC5, RKO, HCT116, LoVo and LS174T cell lines) but not p53$^{mutant}$ (as in mock-transduced LS123, SW620 and HT29 cell lines) transactivated the p21$^{Cip1}$ promoter carried in the tranfected plasmids. Also shown in FIG. 3B are the effects of Ad-KRhdm2 transduction on the p53 transactivating activities. The transactivating activities of p53$^{wild}$ in the cell lines with activating KRAS$^{mutant}$/p53$^{wild}$ cell lines were abolished by transduction of Ad-KRhmd2, of which the Hmd2 expression was up-regulated as shown in FIGS. 2A and C. Compared with the Ad-Δp53REP2 transduced control, Hdm2 expressed in these Ad-KRhdm2-transduced cells is to be responsible for the abolishment of p53 transactivating activity. The transactivation of p21$^{Cip1}$ promoter in cell lines with p53$^{wild}$ was also abolished by Ad-E1 infection but not by Ad-Δp53REP2 infection. The E1b-55kD expressed in the Ad-E1 but not in the Ad-Δp53REP2-transduced cell lines with p53$^{wild}$ is reasoned to responsible for the inhibition of p53 transactivating function.

Example 6

Selective In Vitro Cytopathic Effects of Ad-KRhdm2

Figure 4:
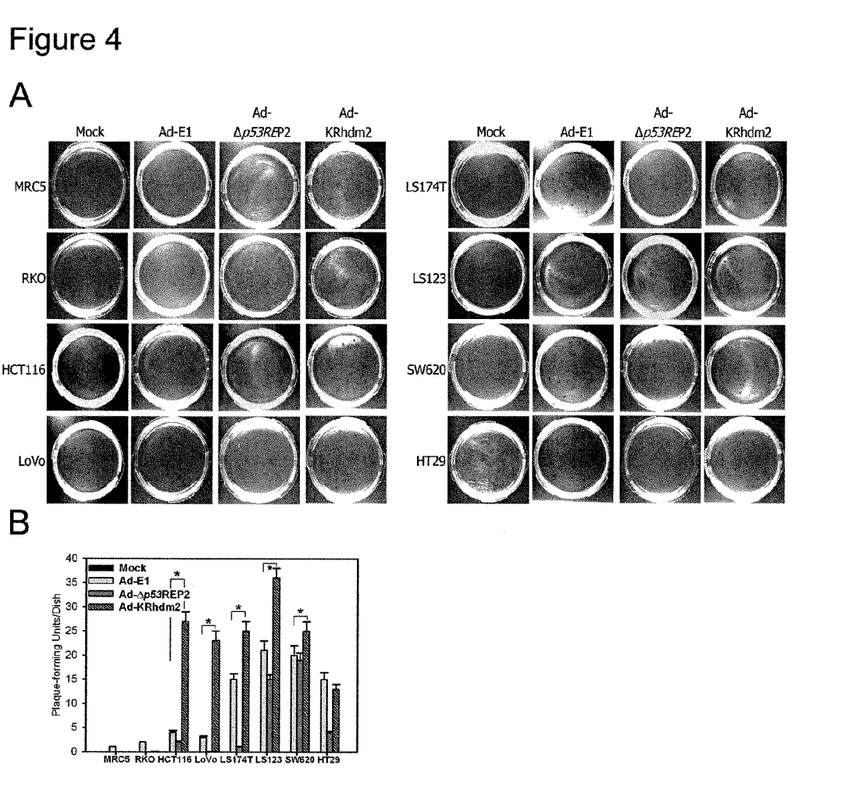

An in vitro plaque-forming assay was preformed to evaluate the cytopathic effect (CPE) of Ad-KRhdm2 on a panel of tumor cell lines and the MRC5 normal cell line. Ad-E1 and Ad-Δp53REP2 were also used for infection in parallel as controls. Cells were infected with Ad-hMDM2 at MOIs of $4\times10^{-5}$ to $4\times10^{-3}$. As shown in FIG. 4, plaque-forming units (pfus) were evaluated 7 days after 1-h infection at MOI of $4\times10^{-4}$. Ad-KRhdm2 formed plaques markedly on HCT116, LoVo, LS174T, LS123, and SW620 cell cultures with activating KRAS$^{mutant}$ (FIGS. 4A and B), irrespective of p53 status. Ad-Δp53REP2 vectors also produced marked plaque formation on cultures of LS123, SW620, and HT29 cell lines, which harbor loss-of function p53 mutations (FIG. 3B and FIG. 4). These cell lines (LS 123, SW620, and HT29) appeared to be more susceptible to Ad-KRhdm2 than to Ad-E1 by having more plaques formed at the same MOI.

Figure 5:
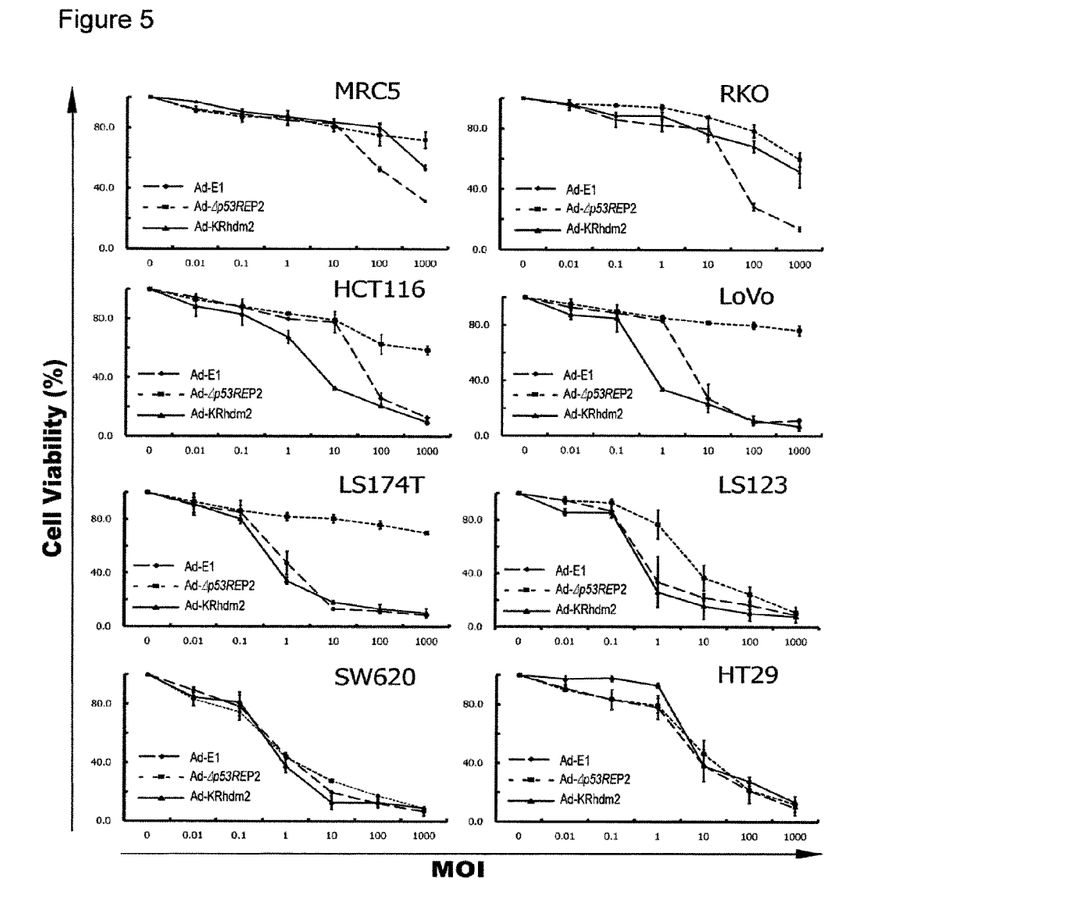
FIG. 5 shows effects on viability of cell lines transduced with Ad-KRhdm2 and controls. For cell viability determination by MTT assay, 10⁴ cells of each cell line were seeded to each well of 96-well plate and infected with Ad-E1, Ad-Δp53REP2, or Ad-KRhdm2 at the indicated MOI (0.01, 0.1, 1, 10, 100, and 1,000). The cell survival was determined after 7 days. Data are presented as mean±SE of triplicates of at least three independent experiments.

For quantification of dose effects, the selective cytopathic effects of Ad-KRhdm2 on cell viability of the cell lines used in plaque-forming assay were also examined. The "CE50" of an Ad vector herein represents the MOI at which infection with the adenoviral vectors leads to decrease of viability to 50% after 7-day incubation. As shown in Table 1 and FIG. 5, the CE50s of Ad-KRhdm2 for the HT116, LoVo, and LS174T cell lines, bearing activating KRAS$^{mutant}$/p53$^{wild}$, are 3.18±0.49, 0.48±0.06, and 0.46±0.03, respectively, which are 440 to 3400-fold less than those of Ad-KRhdm2 for normal fibroblasts (MRC5) and RKO tumor cells, 1,000 to 17,000-fold less than those of Ad-Δp53REP2, and 2 to 11-fold less than those of Ad-E1 for the HT116, LoVo, and LS174T cell lines. Similarly, the CE50s of Ad-KRhmd2 for LS123, SW620, and HT29 cell lines with KRAS$^{mutant}$/p53$^{mutant}$ were 0.41±0.09, 0.53±0.08, and 6.07±0.11, respectively, which are not significantly different from those of Ad-Δp53REP2 or Ad-E1 vectors for these cell lines.

TABLE 1

The CE50s of Adenoviral vectors for the cell lines.

| Cell Line | Adenovirus | | |
|---|---|---|---|
| | Ad-E1 | Ad-Δp53REP2 | Ad-KRhdm2 |
| MRC5 | 136.26 ± 17.61 | 8,187.00 ± 860.95 | 1,396.26 ± 181.94 |
| RKO | 38.16 ± 2.31 | 1,926.00 ± 100.26 | 1,571.25 ± 254.24 |
| HCT116 | 34.54 ± 8.11 | 3,168.75 ± 246.28 | 3.18 ± 0.49 |
| LoVo | 4.08 ± 0.52 | 8,201.67 ± 853.04 | 0.48 ± 0.06 |
| LS174T | 0.92 ± 0.16 | 4,239.50 ± 869.03 | 0.46 ± 0.03 |
| LS123 | 0.60 ± 0.07 | 4.95 ± 0.88 | 0.41 ± 0.09 |
| SW620 | 0.71 ± 0.01 | 0.62 ± 0.03 | 0.53 ± 0.08 |
| HT29 | 5.72 ± 0.69 | 9.15 ± 1.49 | 6.07 ± 0.11 |

The result are expressed as mean ± standard deviation (n = 8)

Example 7

Figure 6:
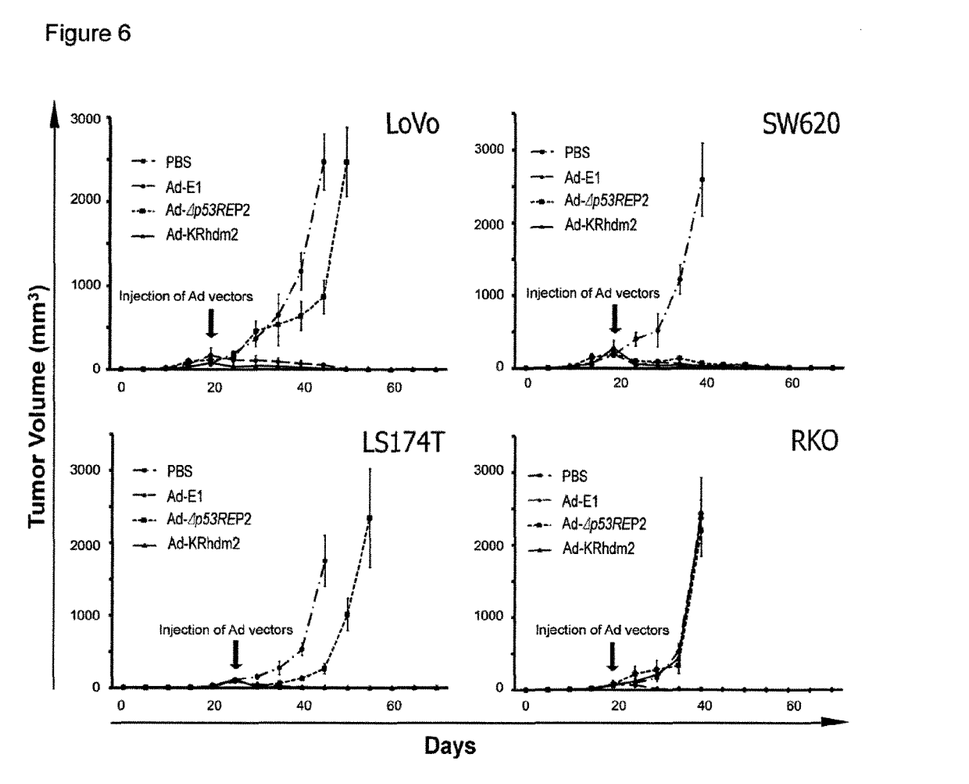

Tumorocidal Effects of Ad-KRhdm2 in Activating KRAS$^{mutant}$ Tumor Xenograft Model Tumor volumes of 8 xenografts from RKO, LoVo, SW620, or LS174T colorectal cancer cell lines assigned to one of the four treatment groups (intratumoral injections of PBS, Ad-KRhdm2, Ad-Δp53REP2 and Ad-E1 vectors) were monitored and plotted against time schedule as shown in FIG. 6.

None of the mice in all treatment groups died even when the tumor volumes reached 2500 mm$^3$. The body weights of mice on day 1 for tumor injection ranged from 16.0 to 19.2 gm. Weight gain was observed in mice in all four treatment groups on day 70 with body weights ranging from 17.8 to 19.6 gm. The body weight gain did not show significant difference between the control group (injected with PBS) and the groups injected with Ad-KRhdm2, Ad-Δp53REP2, or Ad-E1 vectors. Mice were sacrificed when the tumors were too large to bear (around 2500 mm$^3$).

At the end point of the study on Day 70, all the 8 sites inoculated with each of the LoVo, SW620, and LS174T cell lines were tumor free after Ad-KRhdm2 injection (FIG. 6). Meanwhile, on Day 70, all the 8 sites inoculated with SW620 or LS174T cell line were also tumor free after Ad-Δp53REP2 injection. However, RKO tumor xenografts in nude mice kept growing and made no significant difference among tumor volumes of the 4 groups treated with PBS, Ad-Δp53REP2, Ad-KRhdm2, and Ad-E1 on day 40 when the tumor growth reached the maximum. Ad-KRhdm2 thus exhibited selective tumorocidal efficacy in LoVo, SW620 and LS174T tumor xenografts with activating KRAS$^{mutant}$, irrespective of p53 status while Ad-Δp53REP2 exhibited selective tumorocidal efficacy in SW620 and LS 174T tumor xenografts with p53$^{mutant}$.

REFERENCES

1. Alemany R, Balague C, Curiel D T. Replicative adenoviruses for cancer therapy. Nat Biotechnol 2000; 18:723-7.
2. Heise C, Kirn D H. Replication-selective adenoviruses as oncolytic agents. J Clin Invest 2000; 105:847-51.
3. Alemany R. Designing adenoviral vectors for tumor-specific targeting. Methods Mol Biol 2009; 542:57-74.
4. DeWeese T L, van der Pod H, Li S, et al. A phase I trial of CV706, a replication-competent, PSA selective oncolytic adenovirus, for the treatment of locally recurrent prostate cancer following radiation therapy. Cancer Res 2001; 61: 7464-72.
5. Khuri B R, Nemunaitis J, Ganly I, et al. A controlled trial of intratumoral ONYX-015, a selectively-replicating adenovirus, in combination with cisplatin and 5-fluorouracil in patients with recurrent head and neck cancer. Nat Med 2000; 6:879-85.
6. Nemunaitis J, Ganly I, Khuri F, et al. Selective replication and oncolysis in p53 mutant tumors with ONYX-015, an E1 B-55 kD gene-deleted adenovirus, in patients with advanced head and neck cancer: a phase II trial. Cancer Res 2000; 60:6359-66.
7. Chu R L, Post D E, Khuri F R, Van Meir E G. Use of replicating oncolytic adenoviruses in combination therapy for cancer. Clin Cancer Res 2004; 10:5299-312.
8. Bischoff J R, Kirn D H, Williams A, et al. An adenovirus mutant that replicates selectively in p53-deficient human tumor cells. Science 1996; 274:373-6.
9. Heise C C, Williams A M, Xue S, Propst M, Kirn D H. Intravenous administration of ONYX-015, a selectively replicating adenovirus, induces antitumoral efficacy. Cancer Res 1999; 59:2623-8.
10. Goodrum F D, Ornelles D A. The early region 1B 55-kilodalton oncoprotein of adenovirus relieves growth restrictions imposed on viral replication by the cell cycle. J Virol 1997; 71:548-61.
11. Steegenga W T, Riteco N, Bos J L. Infectivity and expression of the early adenovirus proteins are important regulators of wild-type and DeltaE1 B adenovirus replication in human cells. Oncogene 1999; 18:5032-43.
12. Chan T L, Zhao W, Leung S Y, Yuen S T. BRAF and KRAS mutations in colorectal hyperplastic polyps and serrated adenomas. Cancer Res 2003; 63:4878-81.
13. Eberhard, D A, Johnson, B E, Amler, L C, et al. Mutations in the epidermal growth factor receptor and in KRAS are predictive and prognostic indicators in patients with non-small-cell lung cancer treated with chemotherapy alone and in combination with erlotinib. J Clin Oncol 2005; 23:5900-9.

14. Zhang H, Rosdahl I. Expression of oncogenes, tumour suppressor, mismatch repair and apoptosis-related genes in primary and metastatic melanoma cells. Int J Oncol 2001; 19:1149-53.
15. Rothmann T, Hengstermann A, Whitaker N J, Scheffner M, zur Hausen H. Replication of ONYX-015, a potential anticancer adenovirus, is independent of p53 status in tumor cells. J Virol 1998; 72:9470-8.
16. Chen J, Lin J, Levine A J. Regulation of transcription functions of the p53 tumor suppressor by the mdm-2 oncogene. Mol Med 1995; 1; 142-52.
17. Phelps M, Darley M, Primrose J N, Blaydes J P. p53-independent activation of the hdm2-P2 promoter through multiple transcription factor response elements results in elevated hdm2 expression in estrogen receptor alpha-positive breast cancer cells. Cancer Res 2003; 63:2616-23.
18. Ries S, Biederer C, Woods D, et al. Opposing effects of Ras on p53: transcriptional activation of mdm2 and induction of p19ARF. Cell 2000; 103:321-30.

What is claimed is:

1. An isolated nucleic acid promoter comprising the nucleic acid sequence as shown in SEQ ID NO: 2 (Δp53REP2 promoter).

2. A conditionally-replicative adenoviral vector, comprising Δp53REP2 promoter of claim 1, Hdm2-encoding DNA located at downstream of and operably linked to the Δp53REP2 promoter and the encoding DNAs of E1A and E1B-19 kD but not E1B-55 kD.

3. The vector of claim 2, which can be used in combination with radiation therapy or chemotherapy.

4. The vector of claim 2, which is tumor-selective.

5. A pharmaceutical composition, comprising a vector of claim 1 and pharmaceutically acceptable carriers.

6. The pharmaceutical composition of claim 5, which is used in the treatment of cancers.

7. The pharmaceutical composition of claim 6, wherein the cancer is selected from the group consisting of myeloid lymphomas, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leimyosarcoma, rhabdotheliosarcoma, colon carcinoma, pancreatic cancer, liver cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependynoma, pinealoma, hemangioblastoma, retinoblastoma, leukemia (e.g. acute lymphocytic leukemia), acute myelocytic leukemia (myelolastic, promyelocytic, myelomonocytic, monocytic and erythroleukemia), chronic leukemia (chronic myelocytic (granulocytic) leukemia and chronic lymphocytic leukemia), polycythemia vera, lymphoma (Hodgkin's disease and non-Hodgkin's diseases), multiple myeloma, Waldenstrom's macroglobulinemia, rectal carcinoma, head and neck cancer, brain cancer, cancers of unknown primary site, cancers of the peripheral nervous system, cancers of the central nervous system, acoustic neuroma, oligodendroglioma, meningioma, neuroblastoma, heavy chain disease, metastases, and any disease or disorder characterized by uncontrolled or abnormal cell growth.

* * * * *